(12) United States Patent
Neef et al.

(10) Patent No.: US 8,753,583 B2
(45) Date of Patent: Jun. 17, 2014

(54) APPARATUS FOR HANDLING SPECIMEN SLIDES

(75) Inventors: Bernhard Neef, Nussloch (DE); Simon Keimer, Leimen (DE); Karl-Heinz Westerhoff, Eppingen (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 244 days.

(21) Appl. No.: 13/304,431

(22) Filed: Nov. 25, 2011

(65) Prior Publication Data

US 2012/0134894 A1    May 31, 2012

(30) Foreign Application Priority Data

Nov. 26, 2010 (DE) .......................... 10 2010 060 825

(51) Int. Cl.
*B01L 3/00* (2006.01)

(52) U.S. Cl.
USPC ............ 422/500; 422/536; 422/560; 422/563

(58) Field of Classification Search
USPC ................ 422/63–67, 536, 50, 500, 560, 563
See application file for complete search history.

(56) References Cited

U.S. PATENT DOCUMENTS

| | | | |
|---|---|---|---|
| 2004/0002163 | A1 | 1/2004 | Reinhardt et al. |
| 2005/0186114 | A1* | 8/2005 | Reinhardt et al. .............. 422/65 |
| 2006/0231023 | A1 | 10/2006 | Angros |
| 2007/0172911 | A1 | 7/2007 | Farrell et al. |
| 2009/0110597 | A1 | 4/2009 | Ljungmann et al. |

FOREIGN PATENT DOCUMENTS

EP    1717571    11/2006

* cited by examiner

*Primary Examiner* — Jyoti Nagpaul
(74) *Attorney, Agent, or Firm* — Hodgson Russ LLP

(57) ABSTRACT

An apparatus (10) for handling specimen slides (32, 78, 80) has at least one coverslipping module (14) for coverslipping thin sections arranged on specimen slides (32, 78, 80). The apparatus (10) further encompasses a drying unit (16, 70, 90) for extracting solvent from the mounting medium applied onto the specimen slides (32, 78, 80). The drying unit (16, 70, 90) has an air delivery unit (40) for delivering an air flow to the specimen slides (32, 78, 80).

16 Claims, 8 Drawing Sheets

APPARATUS FOR HANDLING SPECIMEN SLIDES

CROSS REFERENCE TO RELATED APPLICATIONS

This application claims priority of German patent application number 10 2010 060 825.4 filed Nov. 26, 2010, the entire disclosure of which is incorporated by reference herein.

FIELD OF THE INVENTION

The present invention relates to an apparatus for handling specimen slides that encompasses at least one coverslipping module for coverslipping thin sections arranged on the specimen slides.

BACKGROUND OF THE INVENTION

In histology, thin sections generated from tissue samples are mounted onto specimen slides. The thin sections mounted onto the specimen slides are then usually treated, for example stained and/or dewatered. The thin section is then covered with a coverslip in order to protect the thin sections. Prior to mounting of the coverslip, a mounting medium, by way of which the coverslip adheres to the specimen slide, is first applied. The coverslipped specimen slides are then delivered to a microscope.

A problem with known apparatuses for coverslipping thin sections arranged on specimen slides is that the coverslipped specimen slides must be handled very carefully, since upon removal of the specimen slides from the coverslipping module, the mounting medium has not yet dried and the coverslip can slip off if the specimen slides are not held horizontally. The thin section can thereby be damaged. It is likewise possible for the coverslip, as a result of slippage, to protrude laterally beyond the specimen slide, so that a person handling the specimen slide can easily cut him- or herself thereon. This is problematic in particular when handling contaminated thin sections, since the operator is then exposed to a risk of infection.

The document US 2009/0110597 A1 discloses an apparatus for handling specimen slides that encompasses a coverslipping module, a drying unit, and an output unit for outputting the coverslipped and dried specimen slides. Here the specimen slides are dried while they are being individually transported through the drying unit to the output unit, and are deposited individually in the output unit.

Further apparatuses and methods for coverslipping specimen slides are known from the documents US 2007/0172911 A1 and US 2006/0231023 A1.

SUMMARY OF THE INVENTION

It is an object of the invention to describe an apparatus for handling specimen slides with which thin sections arranged on the specimen slides can be coverslipped in simple fashion in such a way that the coverslipped specimen slides can easily be handled.

This object is achieved by an apparatus having the features described herein. Advantageous embodiments of the invention are indicated in the present specification.

The result of providing a drying unit for extracting solvent from the mounting medium applied onto the specimen slides is that the mounting medium dries out quickly, and the coverslipping means thus adheres firmly to the specimen slide. The specimen slide can thus already be removed shortly after coverslipping, such that the coverslipping means cannot slip off even if the specimen slide is held askew. Glass coverslips are used, in particular, as coverslipping means. The solvent encompasses, in particular, xylene, toluene, and/or water.

Extraction of solvent from the applied mounting medium is achieved by delivering an air flow to the specimen slides through an air delivery unit of the drying unit. This air drying results in low-stress drying of the mounting medium, so that the thin sections mounted onto the specimen slides are not damaged. In particular, this ensures that a temperature at which the thin sections might be damaged is not reached during drying.

The apparatus encompasses in particular a transport unit with which the coverslipped specimen slides can be transported from the coverslipping module to the drying unit. Automatic transportation of the coverslipped specimen slides from the coverslipping module to the drying unit is thus provided, so that manual intervention can be dispensed with and there is assurance that as a result of transport using the transport unit, the horizontal position of the specimen slides is maintained during transport and slippage of the coverslips is avoided.

The specimen slides are received during transport, in particular, in one or more racks, so there is no need to transport each specimen slide individually. The result thereby achieved is that more specimen slides can be transported per unit of time. In addition, the handling of racks is simpler than the handling of individual specimen slides, in particular when the mounting medium is not yet dry. The specimen slides with the thin sections mounted onto them are preferably also introduced in racks into the apparatus via an input tray, and transported in the rack to the coverslipping module. After coverslipping, the coverslipped specimen slides are transported back into the rack before the latter is transported by the transport unit to the drying unit. After drying of the mounting medium in the drying unit, the racks are transported with the aid of a transport unit into an output tray, from which the racks are removable in mechanized and/or manual fashion.

In an alternative embodiment of the invention, the specimen slides can also be transported individually from the coverslipping module to the drying unit, and received individually in the drying unit. In addition, it is also alternatively possible for the specimen slides to be transported individually from the input unit to the coverslipping module or from the drying unit to the output tray. It is likewise possible for one portion of the above-described transport operations to occur inside racks, and for the specimen slides to be transported individually during another portion of the above-described transport operations.

The drying unit preferably encompasses a housing that encompasses an opening for delivering and/or removing the racks in which the specimen slides are received. The drying unit is closed off by the housing with respect to the remainder of the apparatus, so that the air flow that is guided along past the specimen slides to be dried cannot escape into the remainder of the apparatus. Simple, targeted drying of the coverslipping media of the specimen slides received in the drying unit is thereby achieved. In addition, the housing protects the specimen slides received in it.

The opening is preferably closable and openable, so that no air flow can escape when the housing is closed. Closure of the opening occurs, in particular, by way of a sliding door, so that little installation space is required, especially compared with a swing-out door. A compact, space-saving configuration of the apparatus is thereby achieved.

In a preferred embodiment of the invention, at least one sub-region of the housing is insulated with the aid of an insulating medium, so that thermal separation is achieved between the interior of the housing and the remainder of the apparatus. It is particularly advantageous if the entire housing is insulated. Additionally or alternatively, the sliding door can also be insulated. Insulation reduces heat losses, so that less energy has to be supplied in order to heat the air flow to a preset temperature.

The drying unit encompasses, in particular, a drying chamber in which at least one rack is receivable. The air delivery unit introduces the air flow into the drying chamber in such a way that the air flow is guided along past the specimen slides received in the rack, so that the solvent is extracted from the mounting medium by the air flow, and the mounting medium dries. It is particularly advantageous if the drying chamber is embodied in such a way that at least two racks are receivable in it, so that a large number of specimen slides can be dried simultaneously in the drying chamber. In an alternative embodiment of the invention, the drying chamber can also be embodied in such a way that more than two racks, in particular three or four racks, are receivable in it.

In this context, the racks are receivable in the drying unit in such a way that the specimen slides arranged in the received rack are arranged horizontally, thereby avoiding slippage of the covering means while the mounting medium has not dried.

The drying unit can furthermore encompass an air discharge unit for discharging air out of the drying chamber. The air flow delivered by the air delivery unit is thereby discharged, thus achieving a continuous flow through the drying chamber and thus a continuous flow of air around the specimen slides.

The air discharge is, in particular, embodied in such a way that it encompasses a fan with which the air to be discharged is aspirated out of the drying chamber. The air delivery unit preferably also encompasses a fan with which the air to be delivered is blown into the drying chamber through a delivery conduit.

In a particularly preferred embodiment of the invention, the air delivery unit delivers to the specimen slides an air flow having a preset temperature. The preset temperature has, in particular, a value between 40° C. and 70° C., preferably between 40° C. and 50° C.

The result of delivering a temperature-controlled air flow is that the heated air can receive more solvent than colder air, in particular air at room temperature, so that the coverslipping media of the specimen slides arranged in the drying chamber dry more quickly, and the time that the specimen slides must spend in the drying chamber is reduced. Delivery of an air flow having a temperature between 40° and 50° ensures on the one hand that rapid drying occurs, and on the other hand that damage to the thin sections due to excessively high temperature is avoided.

To heat the air flow, the drying unit encompasses, in particular, a heating element that heats the air flow before it is delivered to the drying chamber. The heating element is arranged, in particular, at an end of the air delivery unit remote from the drying chamber, so that the greatest possible spacing between the heating element and the drying chamber is achieved. This avoids the possibility that the thin sections mounted onto the specimen slides arranged in the drying unit might be damaged by excessively high temperatures. A particular result of this is that the thin sections are not directly exposed to radiated heat from the heating element.

It is further advantageous if a sensor for ascertaining the actual temperature of the air flow is provided. A control unit compares the actual temperature with a preset temperature, and applies control to the heating element as a function of the result of that comparison so that the delivered air flow has the target temperature. This ensures that the preset target temperature is also reached. Rapid and sufficient drying of the specimen slides is thus achieved, and damage to the thin sections due to excessively high temperatures is avoided. Control is applied to the heating element, in particular, in the form of closed-loop control.

The air delivery unit is embodied in particular in such a way that the air flow has a flow velocity of between 0.5 m/s and 1.5 m/s, and/or a volumetric flow rate of between 4 $m^3/h$ and 5 $m^3/h$. In this case, drying of the coverslipping media sufficient to prevent the coverslips from slipping is achieved within three minutes at an air flow temperature between 50° and 60°, so that the racks received in the drying chamber can be removed after only three minutes. A higher throughput is thereby ensured.

In a particularly preferred embodiment of the invention, the drying unit encompasses at least one sensor with which an actual flow velocity and/or an actual volumetric flow rate are detectable. The control unit compares the ascertained actual flow velocity and/or the ascertained actual volumetric flow rate with a preset target flow velocity or with a preset target volumetric flow rate, respectively, and applies control to the air delivery unit in such a way that an air flow having the preset target flow velocity and/or the preset target volumetric flow rate is guided to the specimen slides. Control is applied, in particular, in the form of closed-loop control.

It is furthermore advantageous if a filter, in particular an activated carbon filter, is used for filtering the air to be delivered. This prevents any modifications, as a result of dirty and/or contaminated air, to the thin sections mounted onto the specimen slides being dried, with the consequence that the subsequent result in the context of microscopy of the thin sections might be incorrect. Additionally or alternatively, a further filter, in particular an activated carbon filter, can be provided in order to filter the discharged air. The result of this is that the air emitted to the environment is not contaminated. This is necessary in particular when the thin sections have such contamination.

The air delivery unit delivers the air flow, in particular, to the drying chamber in a lower region thereof. The result achieved thereby is that the heated air, as it is passed through the drying chamber, can rise from bottom to top in accordance with its natural behavior, so that no (or only a few) means for guiding the air are necessary. Delivery in the lower region of the drying chamber occurs, in particular, at two oppositely located side walls of the drying chamber, while discharge occurs, in particular, centeredly. This causes the air flow to pass in vortex-like fashion through the interstices embodied between two specimen slides arranged adjacent to one another in the rack, so that good drying is achieved within a short time.

In an alternative embodiment of the invention, a respective slit nozzle for delivering the air flow into the drying chamber can be provided on two oppositely located side walls of the drying chamber. The slit nozzles are arranged in such a way that their longitudinal direction extends vertically. The slit nozzles moreover are preferably embodied to be longer than the racks, thereby achieving reliable flow around even the specimen slides at the edge of the rack. Extraction of the air to be discharged occurs in this case in particular in a lower region of the drying chamber.

The air delivery unit has, in particular, at least one delivery conduit for delivering the air flow, and the air discharge unit has at least one discharge conduit for discharging the air that is to be discharged. In a preferred embodiment of the invention, the delivery conduit and the discharge conduit are embodied in such a way that they extend directly next to one another at least in a sub-region, and in particular are embodied integrally in a sub-region of the respective delimiting walls of the discharge conduit and the delivery conduit. A compact, space-saving configuration is thereby achieved.

BRIEF DESCRIPTION OF THE DRAWINGS

Exemplary embodiments of the present invention are described in more detail below with reference to the schematic drawings, in which.

DETAILED DESCRIPTION OF THE INVENTION

Figure 1:
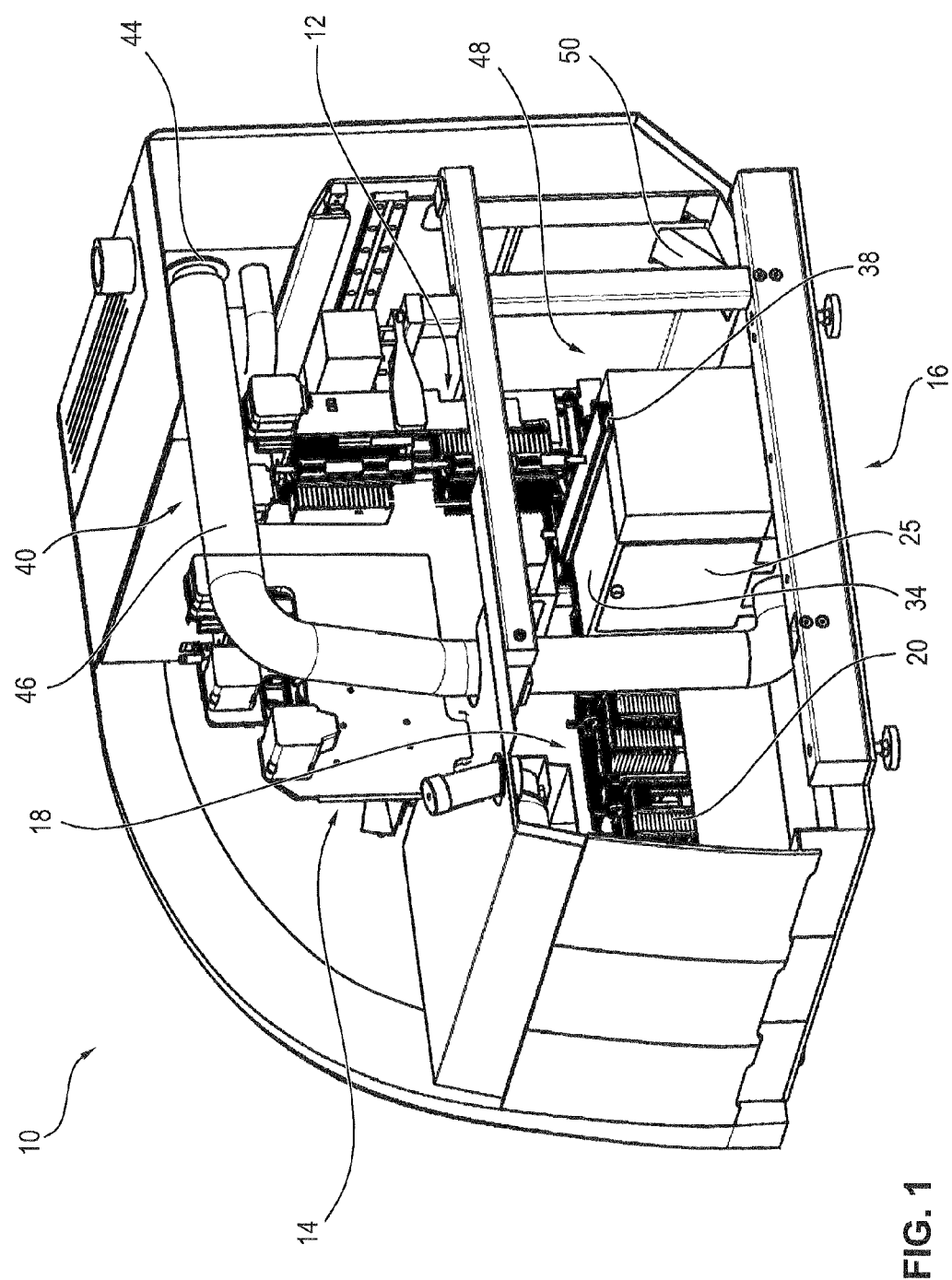
FIG. 1 is a schematic perspective depiction of an apparatus for handling specimen slides.

FIG. 1 is a schematic perspective depiction of an apparatus for handling specimen slides, embodied as a coverslipper 10. Coverslipper 10 encompasses an input unit (not visible in FIG. 1) with which racks, having specimen slides received in them, can be delivered to coverslipper 10. A rack arranged in an output tray is labeled, by way of example, with the reference character 20. Delivery can occur both manually and automatically with the aid of a delivery unit. Both a standalone mode, in which the coverslipper is not connected to further apparatuses for handling specimen slides, and a workstation mode, are thus possible. In workstation mode, coverslipper 10 is arranged, in particular, adjacently to a stainer; once the thin sections arranged on the specimen slides have been stained, the latter, received in racks 20, are automatically transferred from the stainer to coverslipper 20.

Coverslipper 10 further has a transport unit 12 with which racks 20, inputted via the input unit, can be transported to a coverslipping module 14. In coverslipping module 14, the specimen slides are removed individually from rack 20. First a mounting medium is applied onto the specimen slide that has been removed, and then a coverslipping means, in particular a glass coverslip, is mounted onto the mounting medium. The thin section is thereby protected by the coverslip, and a clear presentation is guaranteed upon microscopy of the thin section. Once the thin section on the specimen slide has been coverslipped, the specimen slide is transported back into rack 20 and the next specimen slide is removed for coverslipping.

Once all the specimen slides of rack 20 have been coverslipped, transport unit 12 transports rack 20 into a drying unit 16. In drying unit 16, at least one solvent is at least partly extracted from the mounting medium of the specimen slides received in rack 20, so that the mounting medium dries quickly and the coverslip adheres to the specimen slide. This prevents any possibility of the coverslip slipping when later handled. Damage to the thin section, and injury to the person handling the specimen slides, are thus avoided. Drying unit 16 will be described in further detail in conjunction with the Figures that follow.

Once the specimen slides of rack 20 received in drying unit 20 have been dried, rack 20 is transported by transport unit 12 from drying unit 16 to output tray 18. The latter is embodied in such a way that a plurality of racks 20 are receivable in it. Racks 20 can be removed from output tray 18 manually and/or automatically, before then being delivered to a microscope for microscopy.

Figure 2:
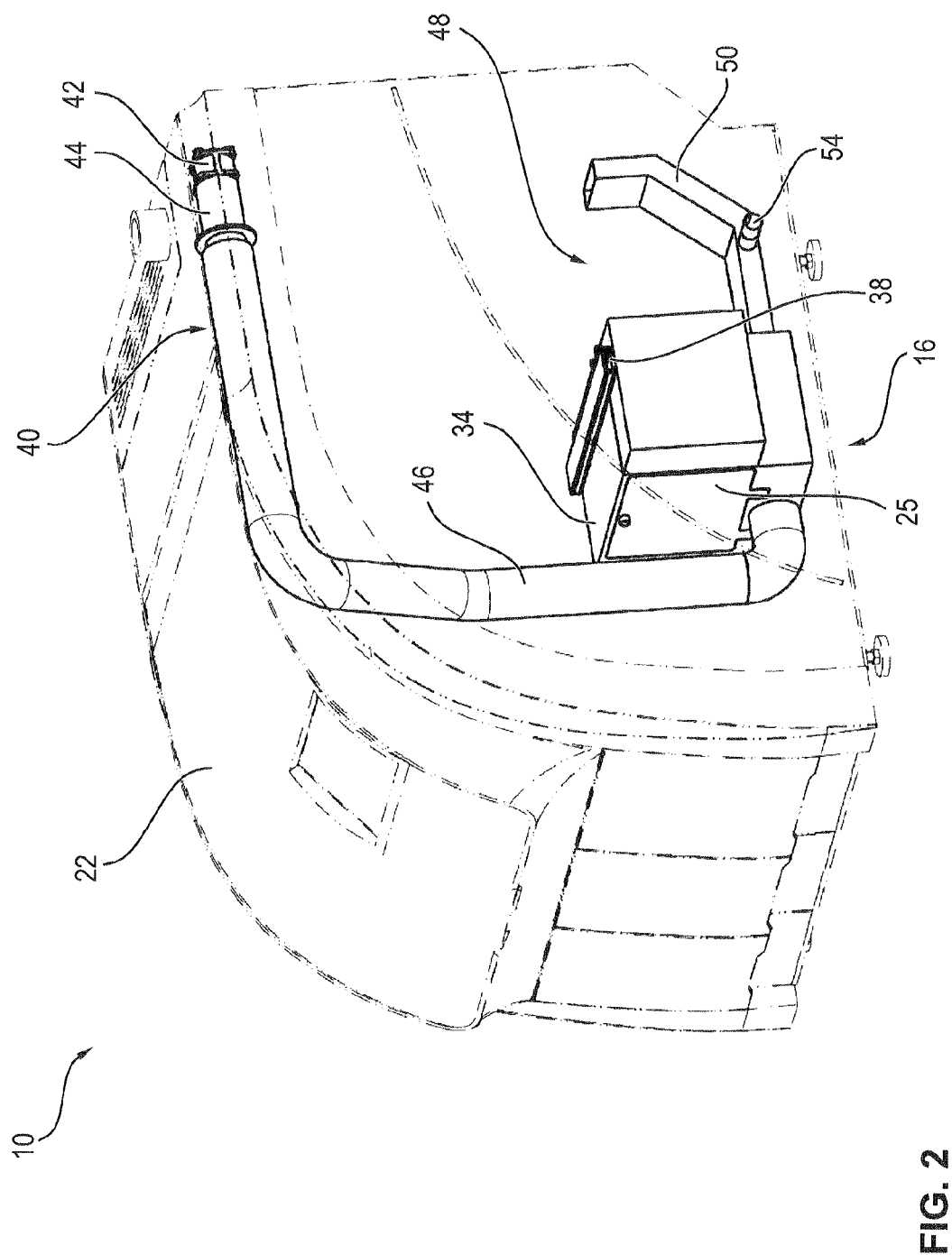
FIG. 2 is a further schematic perspective depiction of the apparatus according to FIG. 1, highlighting the drying unit.

FIG. 2 schematically depicts coverslipper 10 according to FIG. 1 showing only housing 22 of coverslipper 10 and drying unit 16, so that the arrangement of drying unit 16 inside housing 22 becomes visible. The other components of coverslipper 10 are not depicted.

Figure 3:
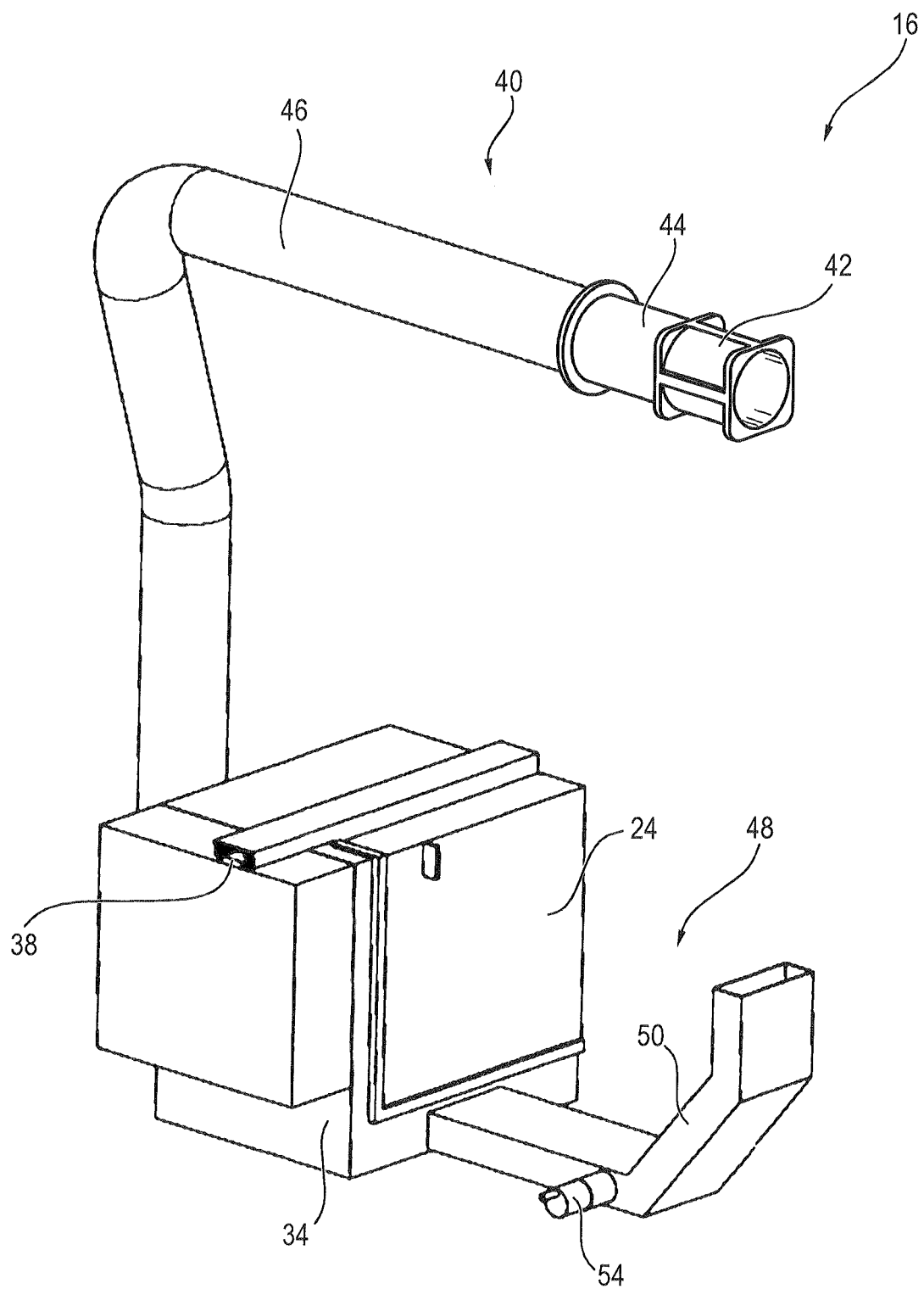
FIG. 3 is a schematic perspective depiction of a drying unit in accordance with a first embodiment of the invention, with the sliding door closed.
Figure 4:
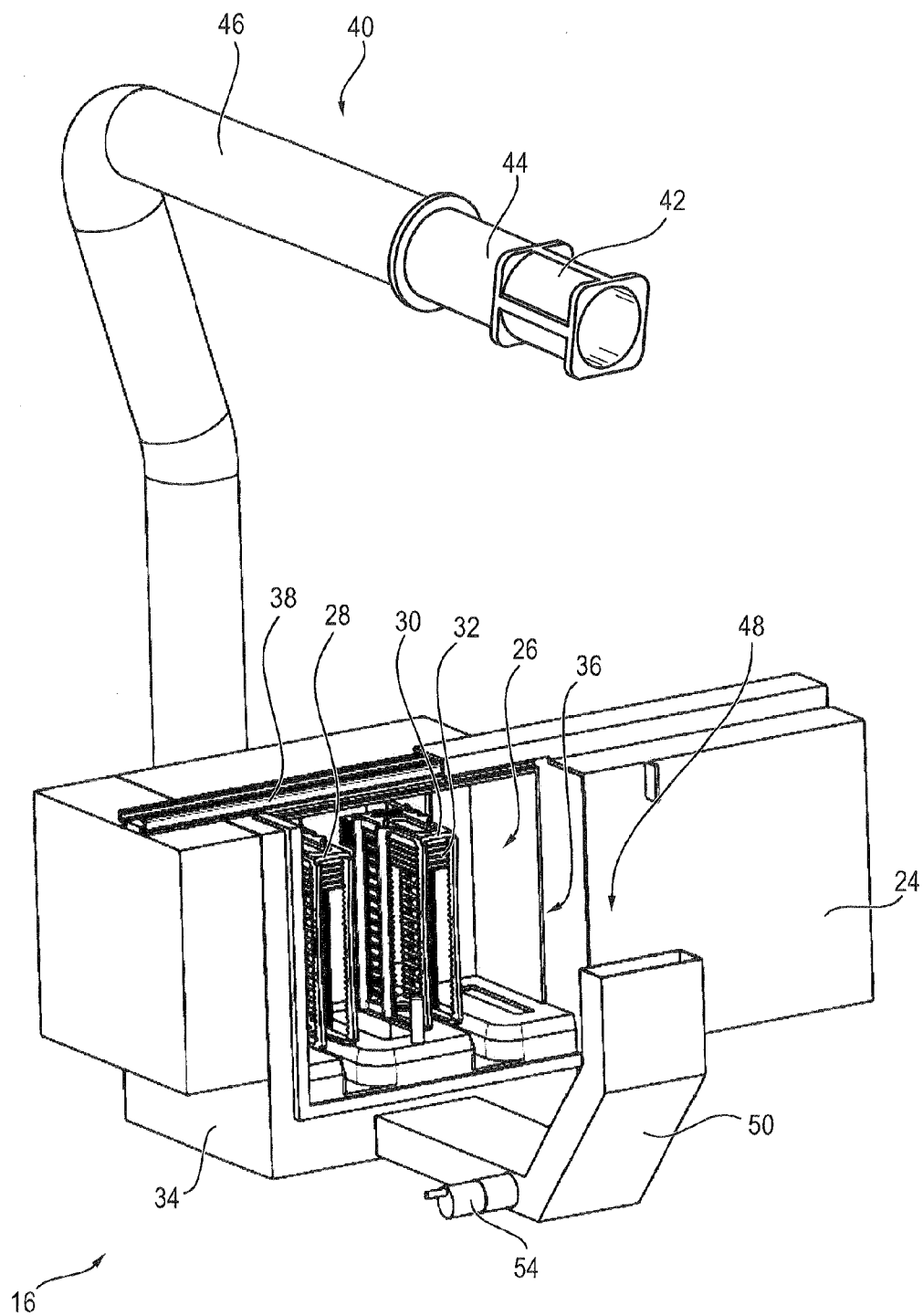
FIG. 4 is a schematic perspective depiction of a drying unit according to FIG. 3, with the sliding door open.
Figure 5:
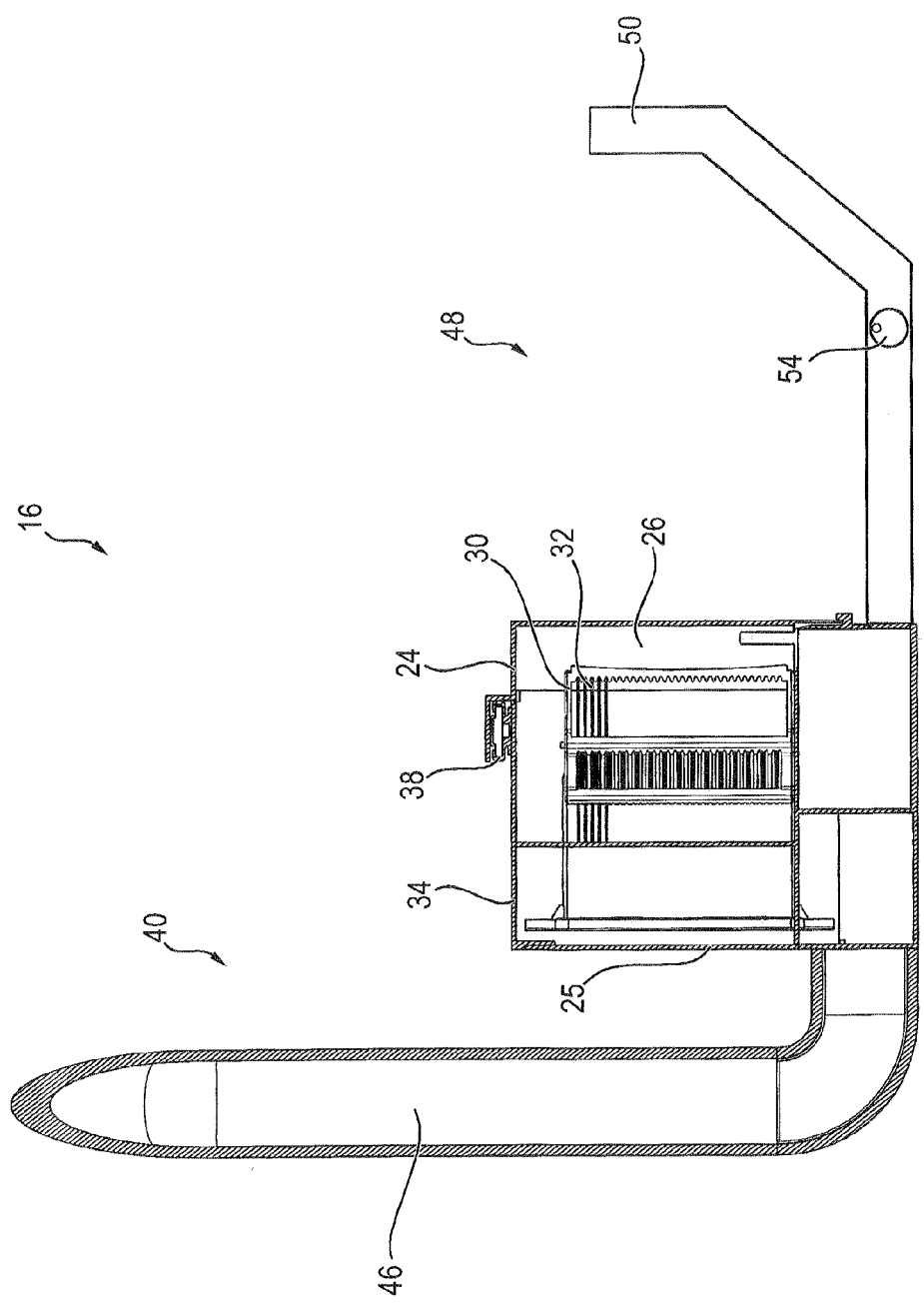
FIG. 5 is a sectioned depiction of the drying unit according to FIGS. 3 and 4.

FIG. 3 is a schematic perspective depiction of drying unit 16 with sliding door 24 closed; in FIG. 4, sliding door 24 is shown open. FIG. 5 is a sectioned depiction of drying unit 16.

Drying unit 16 encompasses a drying chamber 26 in which, in the case of the exemplifying embodiment depicted in FIGS. 1 to 5, two racks 28, 30 are simultaneously receivable. Received in each of racks 28 to 30 is a plurality of specimen slides with mounting medium and coverslips applied, one of these specimen slides being labeled in FIG. 4, by way of example, with the reference character 32. In an alternative embodiment of the invention, drying chamber 26 can also be embodied in such a way that only one rack 28, 30, or more than two racks 28, 30, are receivable in it. Thanks to the capability for receiving two racks 28, 30, a higher throughput of racks 28, 30 and thus of specimen slides 32 can be dried per unit of time, and drying unit 16 can nevertheless be of compact configuration. Drying chamber 26 is surrounding by a housing 34 that delimits drying chamber 26. Housing 34 has an opening 36 through which racks 28, 30 can be delivered by transport unit 12 and removed by transport unit 12. Manual delivery and/or manual removal of racks 28, 30 through opening 36 is alternatively also possible. Opening 36 can be closed off by a sliding door 24 guided via a rail 38. This likewise produces a compact configuration of drying unit 16, since a sliding door 24 of this kind requires less space as compared with a pivotable door. Housing 34 furthermore encompasses a panel 25 (FIGS. 1 and 2) through which, in particular, manual access to drying chamber 26 is possible, for example for maintenance and/or in the event of malfunctions.

Drying unit 16 further encompasses an air delivery unit 40 that delivers an air flow to the drying chamber and thus to specimen slides 32 received in the drying chamber. Solvent is extracted from the mounting medium of specimen slides 32 by the air flow that is guided along past specimen slides 32 and, in particular, surrounds them, thus producing drying of the mounting medium.

Air delivery unit 40 encompasses a fan 42 that draws in ambient air from outside coverslipper 10. A heating element 44 heats the delivered ambient air of the air flow to a preset temperature that, in particular, is higher than the temperature of the air surrounding coverslipper 10. The heated air flow is then delivered via a delivery conduit 46 to drying chamber 26 and thus to specimen slides 32.

Heating element 44 heats the air flow, in particular, to a temperature between 40° C. and 50° C., so that specimen slides 32 are dried in a very short time but damage to the thin sections mounted onto specimen slides 32 due to excessively high temperatures is nevertheless avoided. Heating element 44 is arranged in particular at the end of delivery conduit 46 remote from drying chamber 26, and thus as far away as possible from drying chamber 26. Direct thermal radiation from heating element 44 onto the thin sections is avoided by the large distance between heating element 44 and drying chamber 26, so that damage to the thin sections is prevented.

In an alternative embodiment of the invention, air delivery unit 40 can also not encompass a heating element 44, and can deliver an air flow having the temperature of the air surrounding coverslipper 10. The result is that a longer time is required for drying the mounting media, but a simpler and more compact configuration of drying unit 16, and a lower energy consumption, are achieved.

Housing 34 is, in particular, embodied in such a way that it has an insulating effect, so that only a small amount of thermal energy escapes from drying chamber 26 through housing 34, and thus only a small amount of energy is needed. For this, housing 34 and/or sliding door 24 are insulated, for example, by way of an insulating medium. Housing 34 encompasses, in particular, polyurethane foam. Additionally or alternatively, air delivery conduit 46 is also insulated, so that the heat losses occurring during transport of the air flow from heating element 44 to drying chamber 26 are also small.

Air delivery unit 40, in particular fan 42, is preferably embodied in such a way that the air flow delivered from it to drying chamber 26 has a flow velocity of between 0.5 m/s and 1.5 m/s, preferably approximately 1 m/s. In addition, air delivery unit 40, in particular fan 42, is embodied in such a way that a volumetric flow rate of between 4 $m^3/h$ and 5 $m^3/h$ is achieved. With the above-described embodiment of air delivery unit 40 and the corresponding air flow, a residence time for racks 28, 30 of approximately three minutes in drying chamber 26 is sufficient for the mounting medium to dry so that after removal, the coverslips cannot slip off specimen slides 32 even if specimen slides 32 are held askew.

In an alternative embodiment of the invention, the flow velocity can also be less than 0.5 m/s or greater than 1.5 m/s. A volumetric flow rate that is less than 4 $m^3/h$ or greater than 5 $m^3/h$ can likewise be generated by air delivery unit 40.

Drying unit 16 further encompasses an air discharge unit 48 that discharges air out of drying chamber 26. The result is to maintain a continuous air flow through drying chamber 26, and to achieve continuous drying of specimen slides 32 received in drying chamber 26. In particular, the cooled moister air is discharged with the aid of air discharge unit 48. Air discharge unit 48 encompasses a discharge conduit 50 through which the air to be discharged is discharged.

Figure 6:
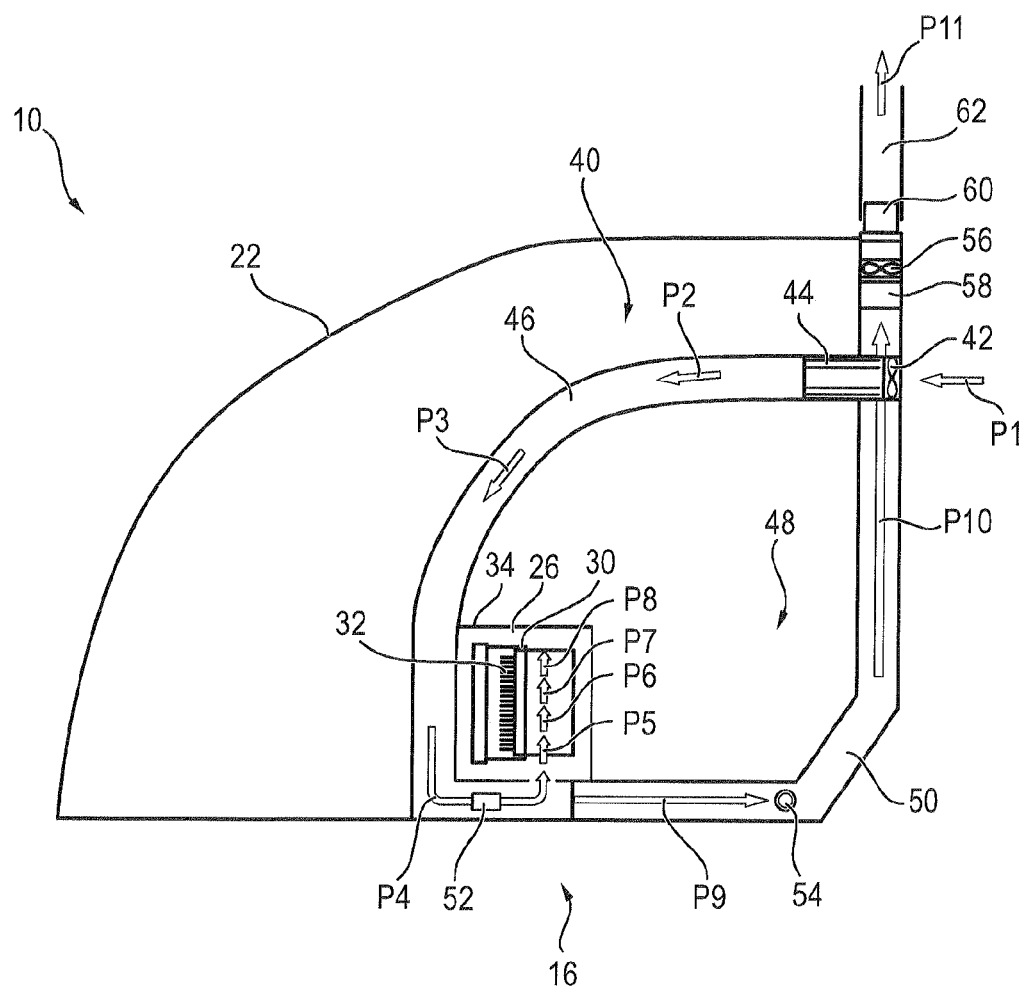
FIG. 6 is a schematic, highly simplified side view of the apparatus according to FIGS. 1 and 2.

FIG. 6 is a schematic and highly simplified side view of coverslipper 10 according to FIGS. 1 and 2, once again depicting only housing 22 and drying unit 16. In FIG. 6 the air flow is depicted by a variety of arrows.

Ambient air, indicated by arrow P1, is drawn in by fan 42 and heated by heating element 44. The heated air is then, as depicted by arrows P2 and P3, transported through delivery conduit 46 to drying chamber 26. At the end of delivery conduit 46 remote from heating element 44, the air is deflected in accordance with arrow P4 so that it is guided into drying chamber 26 laterally from below.

Before the air is guided into drying chamber 26, the actual temperature of the air flow is ascertained with the aid of a sensor 52. A control unit compares the ascertained actual temperature to a preset target temperature, and applies control to heating element 44 as a function of the result of that comparison so that the air flow has the preset target temperature. This control application occurs, in particular, in the form of a control loop.

As indicated by arrows P5 to P8, the warm air rises upward inside drying chamber 26. The air is, in that context, guided in particular in such a way that it is guided between the specimen slides arranged horizontally in racks 28, 30. The air flows around the specimen slides, in particular, in vortex fashion, so that a high level of drying performance is achieved. As it flows around the specimen slides, the air gradually cools and receives evaporated solvent from the mounting medium, so that the mounting medium becomes dried. The cooler air, having a higher solvent concentration, is aspirated centeredly and carried away from drying chamber 26 through discharge conduit 50, in accordance with arrow P9.

Arranged in discharge conduit 50 is a flow sensor 54 with which a determination can be made as to whether an air flow is being guided through discharge conduit 50. Correct operation of drying unit 16 can be monitored in this fashion. A further fan 56, with which the air to be discharged from drying chamber 26 is aspirated, is arranged in exhaust conduit 50. Arranged upstream from further fan 56 is a filter 58 through which the exhaust air, delivered to it in accordance with arrow P10, is filtered. Filter 58 is embodied in particular as an activated carbon filter. Contaminants are removed by filter 48 so that clean exhaust air is discharged.

Arranged at the end of exhaust conduit 50 remote from drying chamber 26 is a connector element 60 with which exhaust conduit 50 can be connected to a central exhaust extraction system 62 of a laboratory in which coverslipper 10 is set up, so that the exhaust air can be directed in accordance with arrow P11, via central exhaust extraction system 62, out of the laboratory and outdoors.

Figure 7:
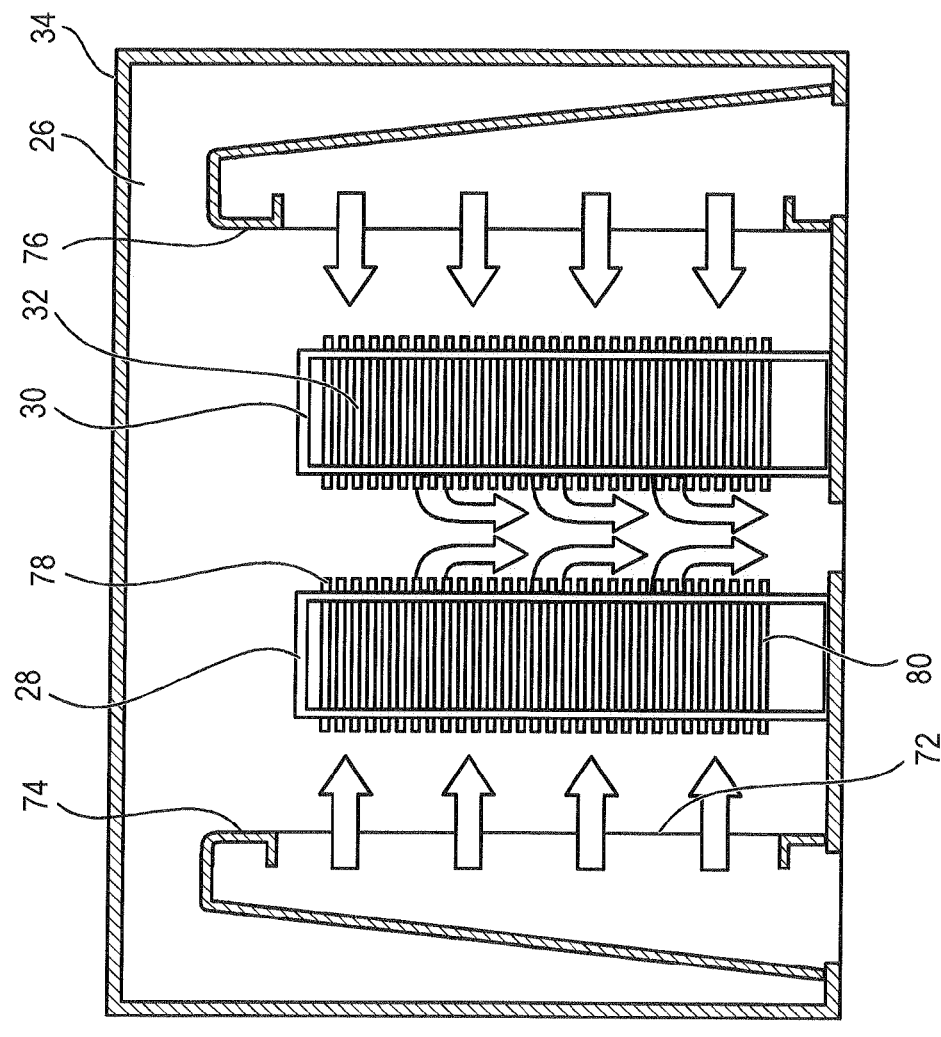
FIG. 7 is a schematic perspective depiction of a drying unit in accordance with a second embodiment of the invention.

FIG. 7 is a portion of a perspective depiction of a drying unit 70 according to a second embodiment of the invention. In this embodiment, drying unit 70 encompasses two slit nozzles 72, which are arranged on two oppositely located side walls 74, 76 and through which the air flow is delivered from air delivery unit 40 to drying chamber 26. Slit nozzles 72 are arranged so that their longitudinal direction extends vertically. Slit nozzles 72 are furthermore embodied so that they are at least as long as the spacing between topmost specimen slide 78 and bottommost specimen slide 80. In a preferred embodiment of the invention, slit nozzle 72 is embodied in such a way that it is a little longer than the spacing between the outermost specimen slides 78, 80 in order to ensure a flow around even the outermost 78, 80 specimen slides.

The result obtained from slit nozzles 72 is that the air flow is guided through specimen slides 78, 80 arranged horizontally in racks 28, 30 so that a sufficient flow of heated air is delivered around specimen slides 78, 80. As the delivered air flows around racks 28, 30, it cools and picks up solvent. After flowing through racks 28, 30, the cooled air drops downward and is aspirated by air discharge unit 48 centeredly in the lower region.

Figure 8:
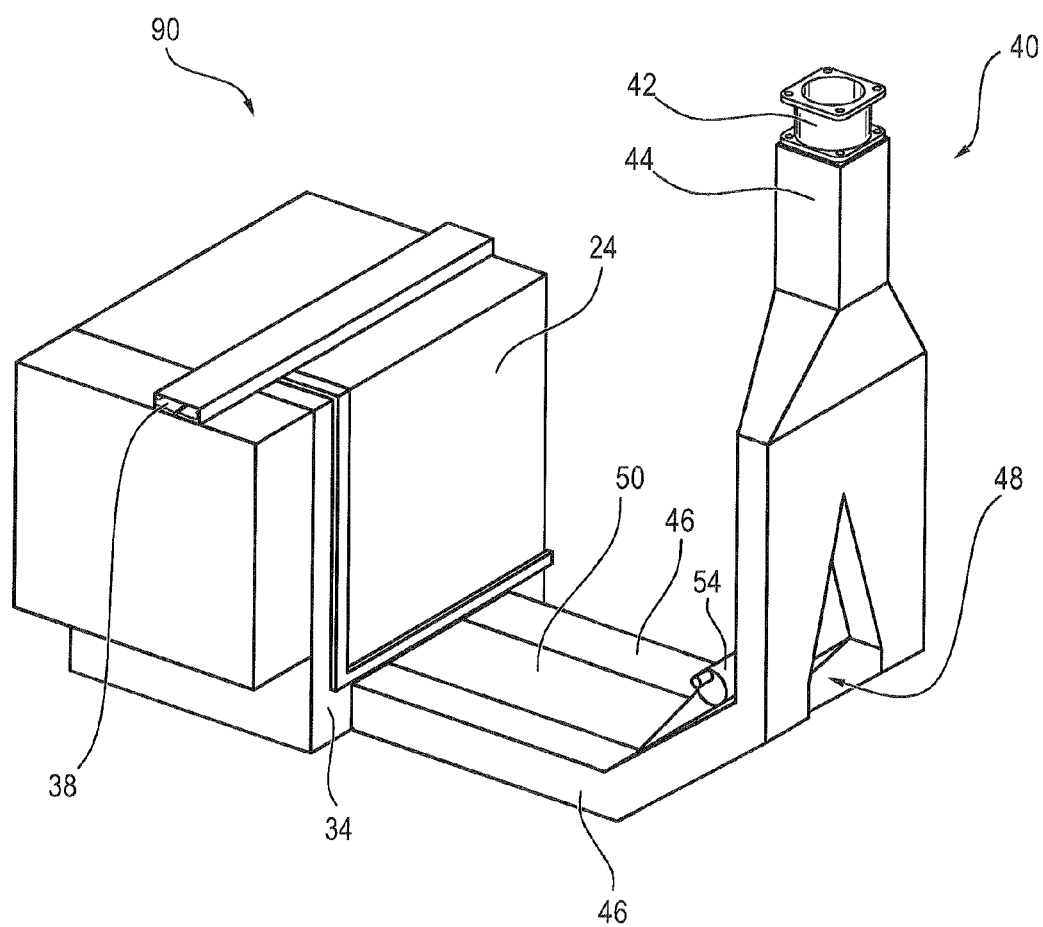
FIG. 8 is a schematic perspective depiction of a drying unit in accordance with a third embodiment of the invention.

FIG. 8 is a schematic perspective depiction of a drying unit 90 according to a third embodiment of the invention. In this third embodiment of the invention, a sub-region of exhaust conduit 50 is arranged between delivery conduit 46. A compact configuration of drying unit 90 is thereby achieved.

The invention is not to be limited to the specific embodiments disclosed, and modifications and other embodiments are intended to be included within the scope of the invention.

List of Reference Numerals

10 Coverslipper
   12 Transport unit
   14 Coverslipping module
   16, 70, 90 Drying unit
   20, 30, 38 Rack
   22 Housing
   24 Sliding door
   25 Panel
   26 Drying chamber
   32, 78, 80 Specimen slides 34 Housing
36 Opening
38 Rail
40 Air delivery unit
42 Fan
44 Heating element
46 Delivery conduit
48 Air discharge unit
50 Discharge conduit
52 Temperature sensor
54 Flow sensor
56 Fan
58 Filter
62 Exhaust extraction system
72 Slit nozzle
74, 76 Side wall
P1 to P11 Air flow

What is claimed is:

1. An apparatus for handling specimen slides, comprising:
at least one coverslipping module (14) for coverslipping thin sections arranged on the specimen slides (32, 78, 80), the at least one coverslipping module (14) configured to apply a mounting medium onto the specimen slide (32, 78, 80) before applying a coverslipping means onto the specimen slide (32, 78, 80);
a drying unit (16, 70, 90) for at least partial extraction of at least one solvent from the mounting medium applied onto the specimen slides (32, 78, 80), the drying unit (16, 70, 90) including an air delivery unit (40) for delivering an air flow to the specimen slides (32, 78, 80);
at least one rack (20, 28, 30) for receiving specimen slides (32, 78, 80); and
a transport unit (12) for transporting the at least one rack (20, 28, 30) having coverslipped specimen slides (32, 78, 80) from the at least one coverslipping module (14) to the drying unit (16, 70, 90);
wherein the drying unit (16, 70, 90) has a drying chamber (26) for receiving the at least one rack (20, 28, 30);
wherein the air delivery unit (40) delivers the air flow into the drying chamber (26), the air delivery unit (40) including at least one delivery conduit (46) for delivering the air flow;
wherein the drying unit (16, 70, 90) includes an air discharge unit (48) for discharging air out of the drying chamber (26), the air discharge unit (48) including at least one discharge conduit (50) for discharging air.

2. The apparatus according to claim 1, wherein the drying chamber (26) is configured to receive at least two racks (20, 28, 30).

3. The apparatus (10) according to claim 1, wherein the drying unit (16, 70, 90) includes a housing (34) having an opening (36) for the delivery or removal of the at least one rack (20, 28, 30) or of the specimen slides (32, 78, 80).

4. The apparatus according to claim 3, wherein the housing further has a sliding door for closing the opening (36).

5. The apparatus (10) according to claim 3, wherein at least a sub-region of the housing (34) is insulated with an insulating medium.

6. The apparatus (10) according to claim 1, wherein the air delivery unit (40) delivers an air flow having a preset temperature.

7. The apparatus (10) according to claim 6, wherein the preset temperature is between 40° C. and 70° C.

8. The apparatus (10) according to claim 6, wherein the air delivery unit (40) includes a heating element (44) for heating the air flow.

9. The apparatus (10) according to claim 8, further comprising:
a sensor (52) for ascertaining temperature of the air flow;
a control unit configured to compare the temperature of the air flow with a preset target temperature, the control being configured to control the heating element (42) as a function of the result of that comparison so that the delivered air flow to the specimen slides has the preset temperature.

10. The apparatus (10) according to claim 6, further comprising a filter for filtering the air flow to the specimen slides.

11. The apparatus (10) according to claim 6, further comprising a filter for filtering the air out of the drying chamber (26).

12. The apparatus (10) according to claim 6, wherein the air delivery unit (40) delivers the air flow to the drying chamber (26) in a lower region of the drying chamber (26).

13. The apparatus (10) according to claim 6, further comprising at least one slit nozzle (72) for delivering the air flow into the drying chamber (26) on two oppositely located side walls (74, 76) of the drying chamber (26).

14. The apparatus (10) according to claim 6, wherein the at least one delivery conduit (46) includes a plurality of delimiting walls, and the at least one discharge conduit (50) includes a plurality of delimiting walls; and
wherein the at least one discharge conduit (50) and the at least one delivery conduit (46) share at least one delimiting wall.

15. The apparatus (10) according to claim 1, wherein the air delivery unit (40) is configured to deliver an air flow having a flow velocity of between 0.5 m/s and 1.5 m/s.

16. The apparatus (10) according to claim 1, wherein the air delivery unit (40) is configured to deliver an air flow having a volumetric flow rate of between 4 m$^3$/h and 5 m$^3$/h.

* * * * *